(12) United States Patent
Mundt et al.

(10) Patent No.: US 7,029,910 B2
(45) Date of Patent: Apr. 18, 2006

(54) IMMUNOGLOBULIN CONTROL REGION

(75) Inventors: Cornelia Anna Mundt, Cambridge (GB); Marianne Brueggemann, Cambridge, MA (US)

(73) Assignee: The Babraham Institute, (GB)

( * ) Notice: Subject to any disclaimer, the term of this patent is extended or adjusted under 35 U.S.C. 154(b) by 51 days.

(21) Appl. No.: 10/081,599

(22) Filed: Feb. 20, 2002

(65) Prior Publication Data

US 2002/0132373 A1    Sep. 19, 2002

(30) Foreign Application Priority Data

Feb. 21, 2001    (GB) .................................... 0104299

(51) Int. Cl.
C12N 15/63    (2006.01)
(52) U.S. Cl. ................... 435/320.1; 536/24.1
(58) Field of Classification Search ............... 536/23.1; 435/320.1
See application file for complete search history.

(56) References Cited

OTHER PUBLICATIONS

Larionov, et al. Highly selective isolation of human DNA from rodent-human hybrid cells as circular yeast artificial chromosomes by transformation-associated recombination cloning. PNAS, 1996, vol. 93, pp. 13925-13930*

Turgeon et al. Isolation and characterization of the human UGT2B15 gene, localized within a cluster of UgT2B genes and pseudogenes on chromosome 4. JMB, 2000. vol. 195, pp. 489-504.*

Burke, David T., Georges F. Carle, Maynard V. Olson (May 1987) "Cloning of Large Segments of Exogenoms DNA into Yeast by Means of Artificial Chromosome Vectors" *Science*236:806-812.

Davies, Nicholas P. and Clare Huxley (1996) "Yac Transfer into Mammalian Cells by Cell Fusion" Chapter 24, in: Methods in Molecular Biology, vol. 54:281292, YAC Protocols, edited by D. Markie Humana Press Inc., Totowa, NJ.

Duff, Karen and Clare Huxley (1996) "Targeting Mutations to YACs by Homologous Recombination" Chapter 18, *In*: YAC Protocols, vol. 54:281-292, edited by D. Markie, Humana Press Inc., Totowa, NJ.

Johnston, John R. (1988) "Yeast genetics, molecular aspects" Chapter 5, *In*: I, Campbell and J.H. Duffus (ed.), Yeast, a practical approach, IRL Press, Oxford, England, p. 107.

Pachnis, Vassilis, Larysa Pevny, Rodney Rothstein, Frank Constantini (Jul. 1990). "Transfer of a yeast artificial chromosome carrying human DNA from *Saccharomyces cerevisiae*into mammalian cells" *Proc. Natl. Acad. Sci. USA*87:5109-5113.

Pavin, William J., Philip Hieter, Roger H. Reeves (Aug. 1990) "Modification and Transfer into an Embryonal Carcinoma Cell Line of a 360-Kilobase Human-Derived Yeast Artificial Chromosome" *Molecular and Cellular Biology*10(8):4163-4169.

* cited by examiner

Primary Examiner—Celine Qian
(74) Attorney, Agent, or Firm—Saliwanchik, Lloyd, & Saliwanchik

(57) ABSTRACT

This invention relates to a control region in human immunoglobulins, to parts thereof and to their use.

3 Claims, 9 Drawing Sheets

A

B

IMMUNOGLOBULIN CONTROL REGION

FIELD OF THE INVENTION

This invention relates to a control region in human immunoglobulins, to parts thereof and to their use.

BACKGROUND OF THE INVENTION

The human IgH locus contains nine functional C genes and two pseudogenes, arranged 5' Cμ-Cδ-Cγ3-Cγ1-ψCε-Cα1-ψCγ-Cγ2-Cγ4-Cε-Cα2 3', over a 350 kb region of chromosome 14 (1). Overlapping phage and cosmid clones established the C gene organisation but attempts to obtain the entire region on overlapping clones or a single yeast artificial chromosome (YAC)[5] have been unsuccessful. PCR-based approaches identified highly repetitive regions downstream of Cα1 and Cα2 which include virtually identical 3' enhancers made up from different numbers of short motifs (3, 4). Similar repetitiveness, leading to instability, was also assumed for the estimated 40–70 kb gap between Cδ and Cγ3, which could not be cloned to establish a C gene contig. Indirect results from transgenic mice lacking different regions 3' of Cμ and Cδ further suggested that this particular downstream region might be important for high expression and switching of IgH genes (5, 6). Analysis of recombination in the Cδ-Cγ3 interval showed a lack of association between these genes, which may indicate a potential hot spot for recombination (7, 8). The potential significance of this region is further supported by the finding that a large area between Cδ and Cγ3 is deleted in certain leukemias, which may be linked to a pathogenic mechanism active at an early stage of B-cell development (9).

In the mouse, the IgH locus has been completely cloned (10) and in DNA-binding assays a cluster of matrix association regions (MARs) was found in the Cδ-Cγ3 intron (11). Although the region was not extensively characterized by sequencing, the presence of long interspersed repetitive elements in the vicinity of MARs may lead to the high recombination observed in this region of the IgH locus. Probes derived from bacteriophage clones covering the mouse Cδ-Cγ3 region failed to identify corresponding sequences in the human locus (9).

During B lymphocyte development it is generally thought that transcriptional activation of the IgH locus is regulated using two enhancer arrays which flank the constant region cluster (12–14, reviewed in 15). These arrays, the Eμ intron enhancer and the 3' enhancer downstream of Cα, contain multiple sites for the binding of both tissue specific and ubiquitous trans-acting factors (13, 16). Enhancer-mediated activation appears to be controlled by the interaction of both negative and positive regulatory elements (17, 18). The Eμ intron enhancer provides potential protein binding sites for several regulatory elements which are essential for lymphocyte differentiation, including E47, PU.1, Ets-1, TFE3, USF and Oct (19, 20). The 3'α enhancer shares some DNA sequence elements with the Eμ enhancer but also has additional motifs for factors involved in transcriptional regulation (13, 16).

Activation and sequential DNA rearrangement of the Ig loci are crucial steps in antibody expression and cis-acting locus elements like enhancers, which accommodate various combinations of factor-binding sites, have been implicated in IgH locus recombination and transcription (17). Although important information about enhancer core functions has been obtained from mutant mouse strains, these are poorly understood processes as there appears to be no activity of either enhancer in early B-cell development when IgH heavy chain rearrangement is initiated. For example, deletion of the heavy chain intron enhancer Eμ showed severe impairment of VH to DJH rearrangement whilst the earlier D to JH rearrangement was much less affected (21). In chimeric mice, in which the Cα3' enhancer was replaced by a marker gene, isotype deficiency and impairment of heavy chain class-switching were observed (18).

SUMMARY OF THE INVENTION

The region between Cδ and Cγ3 of IgH is unstable and may be a recombination hot spot; it has now been shown that 21 kb of the unstable region in the human IgH locus between Cδ and Cγ3 contains a highly clustered array of a large number of transcription factor-binding motifs interspersed with repeat sequences. Transfection assays revealed transcription enhancement and silencing activity at the pre B-cell stage and in transgenic mice strong enhancer function was identified in the bone marrow, the primary site of B-cell differentiation. Flow cytometry analysis of early B-cell populations showed that this enhancer is already active at the pro/pre B-cell stage where DNA rearrangement is initiated. The region accommodating Eδ-γ3 may exert locus control function at an early developmental stage, which may be critical in normal and aberrant B-cell development.

In particular, a pBAC clone (pHuIgH3'δ-γ3) has been isolated, that established a 52 kb distance between Cδ and Cγ3. Sequence analysis identified a high number of repeat elements, explaining the instability of the region, and an unusually large accumulation of transcription factor-binding motifs, both for lymphocyte-specific and ubiquitous transcription activators (IKAROS, E47, Oct-1, USF, Myc/Max), and for factors which may repress transcription (DeltaEF1, Gfi-1, E4BP4, C/EBPbeta). Functional analysis in reporter gene assays revealed the importance of the Cδ-Cγ3 interval in lymphocyte differentiation, and identified independent regions capable of either enhancement or silencing of reporter gene expression, and interaction with the IgH intron enhancer Eμ in transgenic mice. carrying a construct which links the β-globin reporter to the novel δ-γ3 intron enhancer (Eδ-γ3), transgene transcription is exclusively found in bone marrow B-cells from the early stage when IgH rearrangement is initiated up to the successful completion of H and L locus recombination resulting in antibody expression. These findings suggest that the Cδ-Cγ3 interval exerts regulatory control on immunoglobulin gene activation and expression during early lymphoid development.

According to a first aspect of the invention, the Cδ-Cγ3 region is stable in an artificial chromosome or nonhuman animal. It can thus be used to produce a repertoire of human antibodies or antibody fragments in a non-human animal; the functional characteristics of the region, including effective enhancer sequences, can provide a wider and more useful repertoire than has previously been possible.

According to a second aspect of the invention, a functional enhancer and/or silencer sequence within the Cδ-γ3 region (of the human or non-human IgH locus) can be used as such, e.g. in a heterologous construct, to enhance the expression of a heterologous gene. For this purpose, the repeat sequences that give the Cδ-Cγ3 region its instability are not needed.

Products of this invention may have utility in therapy. The utility may be associated with a heterologous gene.

DESCRIPTION OF PREFERRED EMBODIMENTS

Figure 1:
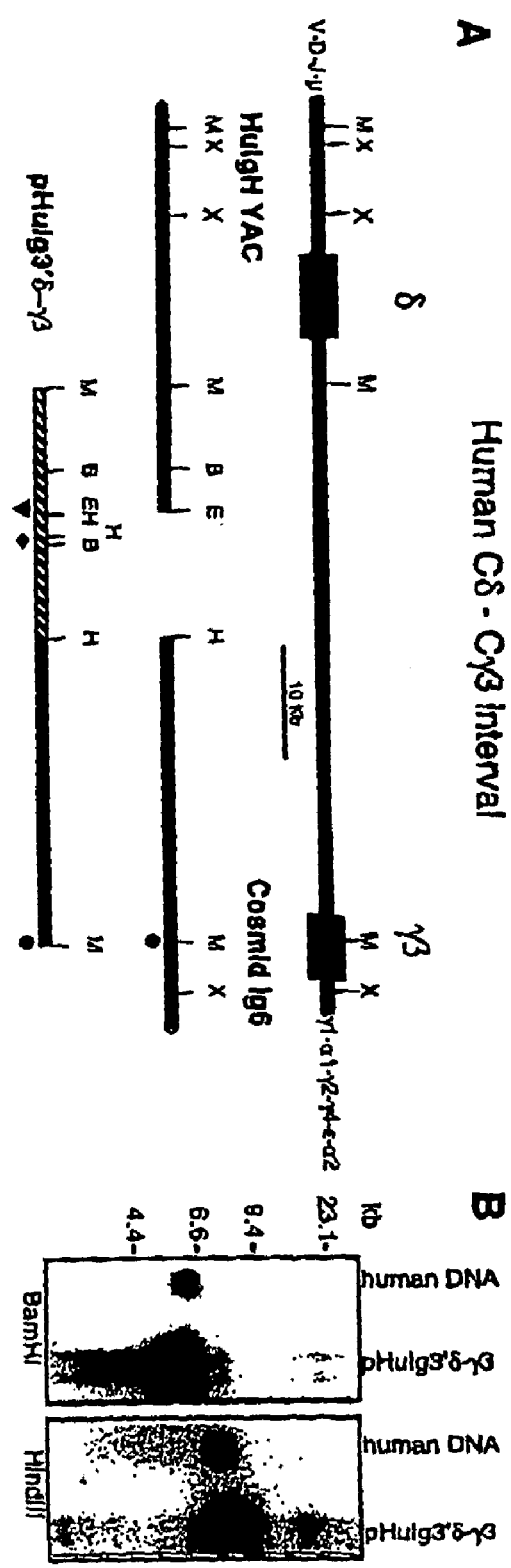
FIG. 1. Location of the pBAC clone pHu3'δ-γ3 spanning the gap in the Cδ-Cγ3 interval region of the human IgH locus. A, Restriction analysis shows that the 48 kb MluI fragment present in pHuIgH3'δ-γ3 (bottom) aligns with the 3' end of the HuIgH YAC (middle, left) and the 5' end of Cosmid Ig6 (middle, right), with the gap indicating the previously uncloned region of the Cδ-Cγ3 Interval (top). The hatched region in pHuIgH3'δ-γ3 was sequenced and fragments were analysed in reporter gene assays M, MluI, X, XhoI; B, BamHI; H, HindIII; E, EcoRI. (▼) 400 bp EcoRI fragment of plasmid pM5-1-23; (●) γ3 gene probe; (♦) 500 bp SspI-BamHI fragment from pHuIgH3'δ-γ3. B, Hybridization of BamHI or HindIII digested human sperm DNA and pHuIgH3'δ-γ3 DNA with the 500 bp SspI-BamHI fragment derived from pHuIgH3'δ-γ3 confirms that the isolated fragment linking the Cδ-Cγ3 gap is in the correct germline configuration.

It will be evident to the skilled person that any suitable artificial chromosome can be used in the invention. Such chromosomes include bacterial, yeast, eukaryotic and mammalian chromosomes.

Similarly, it will be evident that any suitable nonhuman animal can be used for the purposes of producing human antibodies or heavy chains. Such animals include rodents, sheep, horses, pigs, goats, rabbits, chickens and bovine animals.

A chromosome or isolated polynucleotide according to the invention may comprise all or part of the region that has been identified as having functional properties. It will be evident to the skilled person that such functional properties may be characteristic of part only of the whole region. Such parts or fragments can be identified by known means. Similarly, transformation and other techniques that may be required to produce products of the invention are known.

The following description provides illustrative embodiments of the invention. It should not be construed as limiting.

BAC Library Construction

A size-selected library was constructed from human DNA using the pBeloBACII vector (22). A MluI linker was added to the pBeloBACII vector following linearisation with SphI in the multiple cloning site, Human genomic DNA was prepared from the fibroblast cell line KB (23) and digested to completion with MluI. The fragments were size fractionated by Pulsed Field Gel Electrophoresis (PFGE) in 1% low melting temperature agarose (SeaPlaque FCM, USA) at 12V/cm in 0.5×TBE with a 40 sec pulse for 24 h at 3.5° C. Gel slices containing DNA fragments from ~30–80 kb were excised, melted at 67° C. and digested for 1 h at 40° C. with 1 unit Gelase (Epicentre, USA) per 0.1 g of gel. Size-selected DNA (100–200 ng) was ligated with dephosphorylated MluI restricted pBeloBACII vector (25–50 ng) using 4 units T4 ligase (NEB, Canada). Ligation mixtures were dialysed against 3 ml TE and 1 mM polyamines for 4 h at room temperature using Millipore filters 30000 NMWL (Millipore, USA). Aliquots of the dialysed ligation mixture (1 μl) were used to transform E. coli DH10B by electroporation at 120 V, 25 μF, and 100 Ohms (24). Transformed cells were incubated for 90 min at 37° C. in SOC medium, shaking at 250 rpm, and plated on LB-agar containing 12.5 μg/ml chloramphenicol, 50 μg/ml X-Gal, and 25 μg/ml IPTG. Distinguishable white and blue colonies appeared after 24h, and about 5000 white clones were isolated and analysed by colony-filter hybridization with the 0.4 kb EcoRI fragment of pM5-1-23 (25) and human Cγ3 (ref. 26 and see below). The insert size was determined by MluI digest and PFGE.

Hybridization and Sequencing

For hybridization analysis, genomic DNA (10 μg) or pBAC DNA (0.5 ng) was digested with the desired restriction enzyme and separated on 0.8% agarose gels in TAE. DNA was transferred to nylon membranes (Hybond-N, Amersham) by alkaline transfer and the blots were hybridized with oligolabelled probes at 65° C. in Church Buffer. Hybridization probes were a 7.4 kb HindIII fragment containing human γ3 (26) and a 0.4 kb EcoRI fragment obtained from a 3.4 kb BamHI fragment located ~20 Kb downstream of human Cδ from the 3' end of the HuIgH YAC, derived by plasmid rescue after digestion (clone pM5-1-23, ref. 25). The 5.9 kb BamHI fragment of pHuIgH3'δ-γ3 (see FIG. 1) was subcloned and a 0.5 kb SspI-BamHI fragment was derived therefrom for further mapping.

Sequencing was performed using an ABI Model 373 automated sequencer. Sequence information was obtained using vector-specific primers to analyse restriction fragments subcloned in pUC19 or overlapping fragments obtained by exonuclease III digestion of fragments (Erase-a-Base System, Promega, UK), and also by custom oligonucleotides based on initial sequence information.

Cell Lines and Transfection Assay

The cell lines used for the reporter gene analysis were from the Babraham Institute's collection or gift from collaborators and their origin is described in the American Tissue Culture Collection catalog. The human cell lines used were NALM-6 pre B-cells, DG-75 plasma cells, Jurkat T lymphoblast cells and KB fibroblasts (27 and references therein, 28, 29, 23).

The mouse cell lines were 3-1 and 18-81 pre B-cells and the plasma cell lines MPC11 (producing IgG2b) and AH (producing IgM) (30). The cell lines were maintained in RPMI (Gibco, UK) supplemented with 10% FCS and 50 μM β-mercaptoethanol.

Transcriptional activity of fragments from the pHuIg3'δ-γ3 5' region was analysed with a luciferase reporter assay system according to the manufacturer's protocol using a BioOrbit 1253 Luminometer (Promega, UK). The pGL3 vector ensures low background luciferase expression and this allowed the unambiguous measurement of enhancer function. The overlapping fragments from the pHuIg3'δ-γ3 5' region (see FIGS. 1 and 5) tested were: 1) 10.7 kb MluI-HindIII; 2) 7.2 kb MluI-BamHI; 3) 8.5 kb HindIII; and 4) 5.9 kb BamHI. These were inserted 5' of the SV40 promoter of the pGL3 reporter gene construct. The size of fragment 2 in the reporter gene construct was reduced by creating the necessary 5' and 3' overhang by MluI and KpnI restriction and exonuclease III treatment. As a positive control, pGL3 control vector containing the SV40 enhancer was used.

To test the interaction with other IgH enhancers, the human Eμ intron enhancer (25) was added 5' of an inserted fragment Pre B-cells, pro B-cells, Jurkat and KB fibroblasts ($2.5 \times 10^6$) were transfected by electroporation using 7 μg pGL3 containing fragment 1, 2, 3 or 4 with or without Eμ and with 1 μg pSV-β-galactosidase control plasmid as an internal standard. Electroporation conditions were 960μF, 200 Ohms and 270–300V. Cells were harvested after 20–22h incubation. Plasma cells ($1-3 \times 10^5$) were transfected with the above constructs by lipofection with DOTAP (Boehringer, Mannheim, Germany) according to the manufacturer's protocol. The β-galactosidase assay was performed in 100 μl reaction buffer (0.1M $Na_2HPO_4/NaH_2PO_4$ pH7.3; 1 mM MgCl; 50 mM β-mercaptoethanol; 1.33 mg/ml o-nitrophenyl-β-D-galactopyranoside) for 30–120 min. The reaction was stopped with 150 μl 1M $Na_2CO_3$, and the conversion of substrate was measured in a Titertek Multiscan MCC/340 at 410 nm.

Transgene Expression Analysis

The 1.3 kb Eδ-γ3 fragment (position 5885 to 7185 in pGL3) obtained by PCR was added to a 3 kb human β-globin gene subcloned in pUC12 (31) by blunt end ligation into the XbaI site in the linker. A ~4.3 kb SacI-HindIII DNA fragment containing Eδ-γ3 linked to the β-globin reporter gene was gel purified and injected into the pronuclei of fertilised (C57BL/6xCBA)F1 eggs at 1–2 pg/ml (32). Transgenic mice were obtained with high and low copy number verified by tail blot analysis with a transgene probe.

RNA from different tissues was prepared as described by the manufacturer using the RNAqueous Kit (Ambion, UK) or the RNAzol B method (AMS Biotechnology, Oxford, UK) for bone marrow. Cell preparations were essentially free of erythrocytes with the exception of liver cells where a low percentage remained. Hybridization probes were the β-globin transgene and a 540 bp actin gene fragment obtained by PCR (33). For the isolation of B-cell subpopulations by flow cytometry bone marrow cells were stained as described (34). Multicolor staining was carried out with the following reagents in combinations shown in FIG. 7B: PE (phycoerythrin)-conjugated anti-mouse CD25 (P3317, Sigma), PE-conjugated anti-mouse CD45R (B220) (P3567, Sigma), biotinylated anti-mouse IgM (No. 02082D, PharMingen), PE-conjugated anti-mouse c-kit (CD117) (No. 09995B, PharMingen), FIT-conjugated anti-mouse CD19 (No. 09654D, PharMingen), FITC-conjugated anti-mouse IgD (No. 02214D, PharMingen) and biotinylated antimouse CD43 (No. 01602D, PharMingen). Binding of biotinylated antibody was developed with streptavidin quantum red (S2899, Sigma). The oligonucleotides for RT-PCR of β-globin and HPRT as a control have been described (31). RT-PCR was performed with the One-Step System (Gibco-BRL) under the following conditions: 50° C. for 30 min followed by 94° C. for 2 min for cDNA synthesis, followed by 30 PCR cycles (15 sec 92° C., 30 sec 55° C., 30 sec 72° C.) and 5 min at 72° C. to complete the reaction.

The Distance Between Cδ and Cγ3 is 52 kb

Southern blot analysis suggested that the region between Cδ and Cγ3 is 40–70 kb in size (1, 8). We analysed human sperm DNA and the human fibroblast cell line KB (23) by digestion with rare cutting enzymes and hybridization with probes from the 3' end of the human IgH YAC and from human Cγ3 (see FIG. 1). Southern blots of MluI digests showed a possible region of ~50 kb capable of spanning the gap between Cδ-Cγ3 (data not shown). A size-selected bacterial artificial chromosome (BAC) library was constructed and hybridized with the 0.4 kb EcoRI fragment of pM5-1-23, from the 3' end of the IgH YAC (25), and human Cγ3 (26). Of eight clones, pHuIgH3'δ-γ3, hybridized with both of these probes and MluI restriction digestion followed by Pulsed Field Gel Electrophoresis (PFGE) identified a 48 kb insert. Comparison of the restriction patterns of pHuIgH3'δ-γ3 with the HuIgH YAC (5) and cosIg6 (35) revealed substantial homologies at the 5' and 3' ends respectively, which suggested that pHuIgH3'δ-γ3 spanned the gap between the Cδ and Cγ3 constant region genes (FIG. 1A). The 5' MluI cloning site of pHuIgH3'δ-γ3 lies ~4 kb 3' of the δ membrane exon 2, a region not yet characterized by sequence analysis, whilst the 3' MluI cloning site is located in the hinge region of Cγ3 (36). Alignment of restriction maps of pHuIgH3'δ-γ3 with the HuIgH YAC and cosIg6 identified a novel 11 kb region.

To verify that this novel region is in the correct genomic configuration, different digests of human DNA and pHuIgH3'δ-γ3 DNA were analysed in Southern blots using different hybridization probes. An example (FIG. 1B) shows that hybridization with the 0.5 kb SspI-BamHI fragment from pHuIgH3'δ-γ3 identified a 59 kb BamHI fragment and a 8.5 kb HindIII fragment both of which are present in human genomic DNA and pHuIgH3'δ-γ3. The Cδ proximal BamHI site and the Cγ3 proximal HindIII site of the hybridization fragments are also present on the IgH YAC and cos Ig6, respectively. These results confirm that the cloned region on pHuIgH3'δ-γ3 completes the Cδ-Cγ3 sequence gap and establishes the distance between Cδm2 and Cγ3 as 52 kb.

The Cδ-Cγ3 Interval Region is Highly Repetitive

Figure 2:
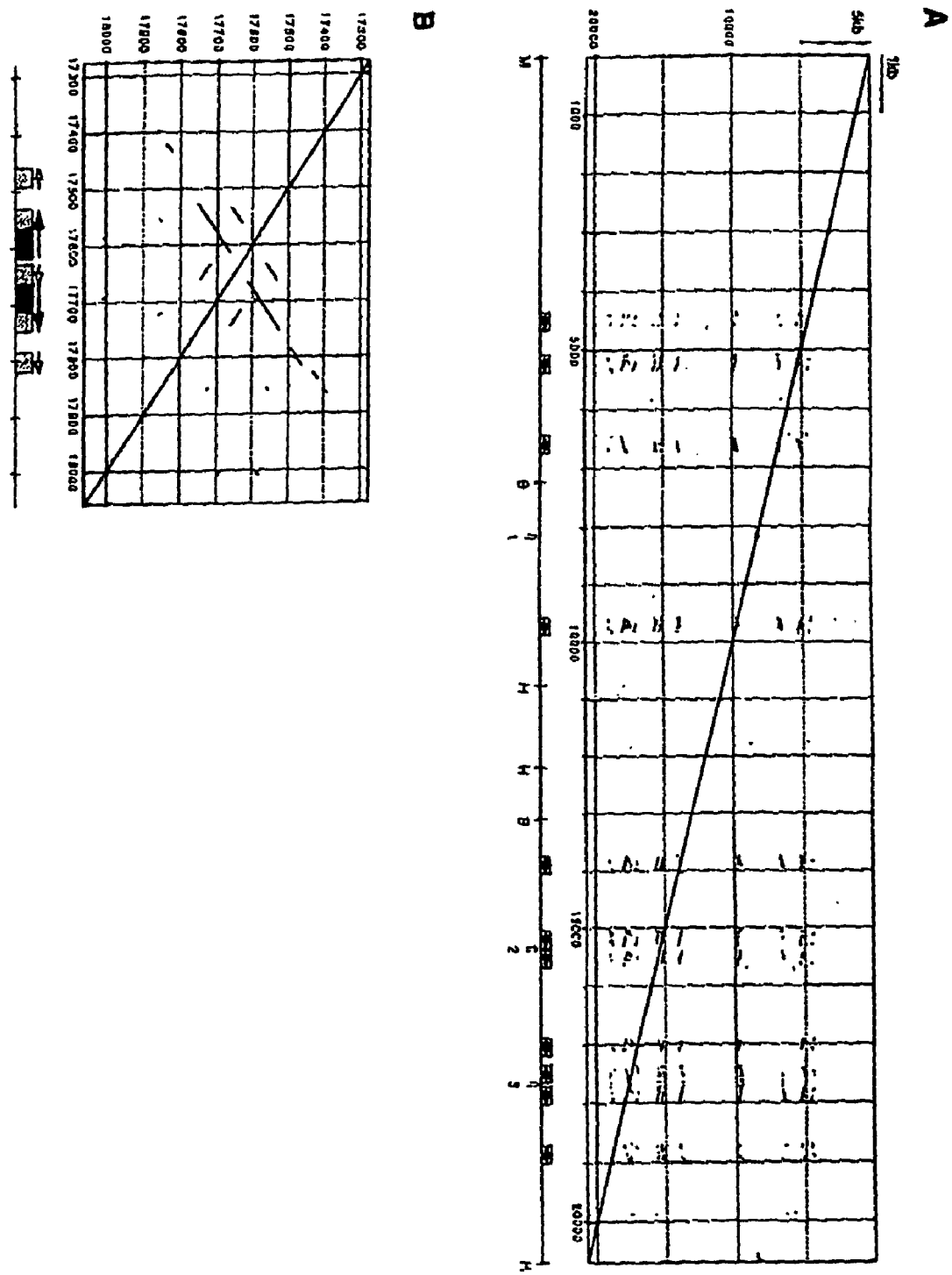
FIG. 2. Analysis of nucleotide sequence of pHuIgH3'δ-γ3. A, Dot Plot of self-alignment of the 5' 21 kb of the cloned region between Cδ and Cγ3 starting at the 5' MluI site (see FIG. 1 for restriction sites) using the MacVector 6.01 program (Oxford Molecular, Oxford, UK). The location of the eleven Alu-repeat-like sequences are indicated as boxes below the matrix with arrows indicating the orientation of the repeal Three other regions of repetitive sequence are indicated by vertical arrows. Region 1 comprises three consecutive MstII-like elements. Region 2 comprises a region of 21 repeats of "CT" followed by 15 repeats of "AT". Region 3 comprises several complete and fragmented Alu motifs, as shown in B. B, Detail of the Alu motifs and fragments in region 3. The orientation of the Alu motif, indicated by a shaded box followed by an unshaded box, is indicated by arrows. The combination of a shaded box followed by an unshaded box forms an Alu-repeat-like element (large filled arrows). Separate unshaded boxes represent incomplete Alu motifs in the orientation indicated.

The nucleotide sequence of the Cδ proximal 5' region of pHuIgH3'δ-γ3 (EMBL no. to be added), indicated in FIG. 1A by the hatched line, was determined by subcloning of overlapping fragments, exonuclease III digestion and primer walking. Self-alignment of this 21 kb region (FIG. 2A) identified many regions of similarity as Alu motifs (37), with a pronounced cluster at the 3' end (FIG. 2B) that incorporated several residual fragments of Alu motifs as well as complete motifs, in various orientations. In addition, we found transposon-like elements (LINE, LTR etc.) in abundance and of different complexity (38–40); three 40 bp MstII-like repeats were arranged in a tandem configuration, which may highlight transposon activity, and a 76 bp region comprising 23 (CT) repeats was followed immediately by 15 (AT) repeats. The CT and AT repeats encode the amino acids pairs Leu/Ser and Ile/Tyr independently of the reading frame. The presence of this large number of repetitive elements may be the reason for the instability of the locus observed during cloning efforts.

A Cluster of Transcription Factor Recognition Motifs

Figure 3:
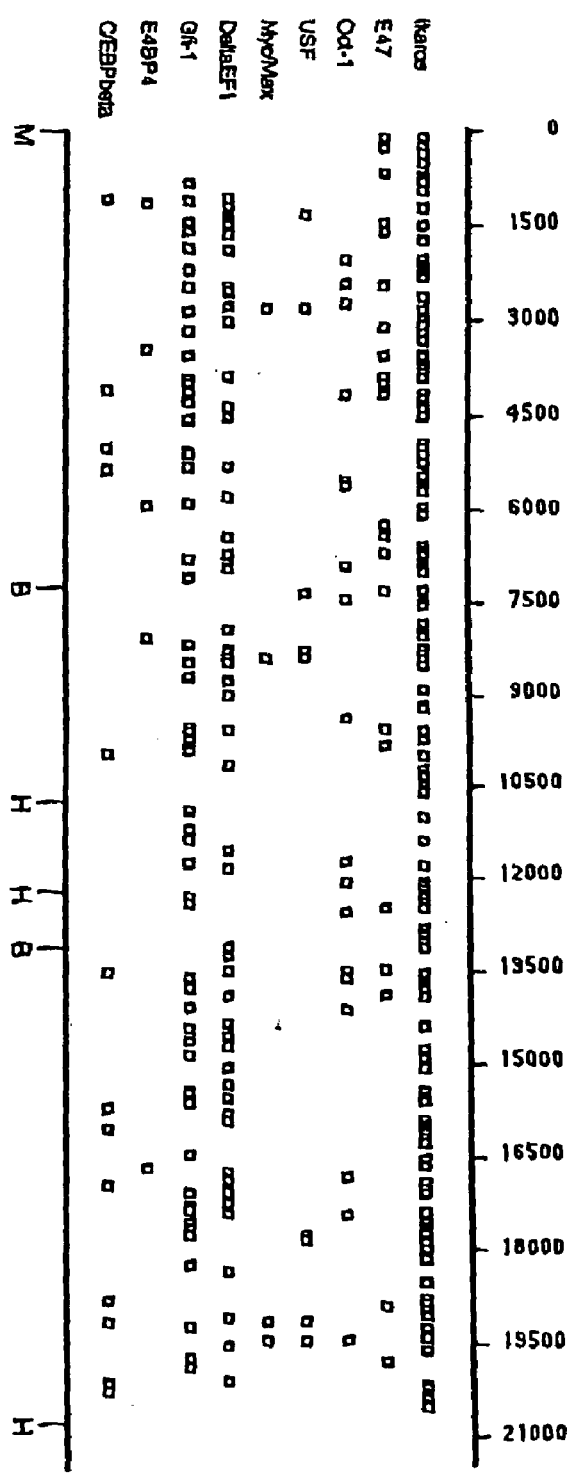
FIG. 3. Location of transcription factor recognition motifs. The sequence of the 5' 20696 bp of the cloned fragment was compared to the TRANSFAC database using Matinspector, with a score of 1.0 for core similarity and ≧0.9 for matrix similarity (41), Restriction sites are indicated for alignment (see FIG. 1); MluI (M), BamHI (B) and HindIII (H). The potential transcription factor-binding sites are indicated by open boxes. Factors which may enhance transcription in lymphocytes include Ikaros (81, 82, 52), E47 (83), Oct-1 (84, 85), USF (45), and Myc/Max (51). Factors which may suppress transcription include DeltaEF1 (56), Gfi-1 (58), E4BP4 (54, 86, 87), and C/EBPbeta (88).

Potential binding factor recognition sites of regulatory proteins were identified by comparison of the pHuIgH3'δ-γ3 sequence with the TRANSFAC transcription-factor database using Matinspector (41, 42). As shown in FIG. 3, many binding motifs were represented very frequently despite the high score used for the database search, which was 10 for core similarity and 0.90 or greater for matrix similarity. The transcription factors identified can operate either to enhance or suppress immunoglobulin transcription, and many are also present in the Eμ and 3'α enhancer regions (reviewed in ref. 43, 44). Binding sites were found for the activating proteins Ikaros, E47, Oct1, USF and Myc/Max (45–51). The Ikaros gene products belong to the group of zinc finger DNA binding proteins (52) and have a complex role in the early stages of lymphocyte development with establishing the maintenance and differentiation of multipotent progenitors (53). In the group of repressor proteins, binding sites for DeltaEF1, Gfi-1, E4BP4 and C/EBPbeta were identified (54–57). The potential binding-site of the nuclear zinc finger protein Gfi-1 (growth factor independence 1) has been identified in a large number of eukaryotic promoter-enhancers (58, 59).

No similar large accumulation of different binding protein recognition sites was evident when other regions of the immunoglobulin H and L chain introns, including known enhancer regions, were examined. The presence of such an extensive and varied cluster of transcription factor-binding motifs may suggest that the region between Cδ and Cγ3 exerts previously unrecognised Ig locus control function.

Pre B-cell Specific Enhancer Activity Downstream of Cδ

Figure 4:
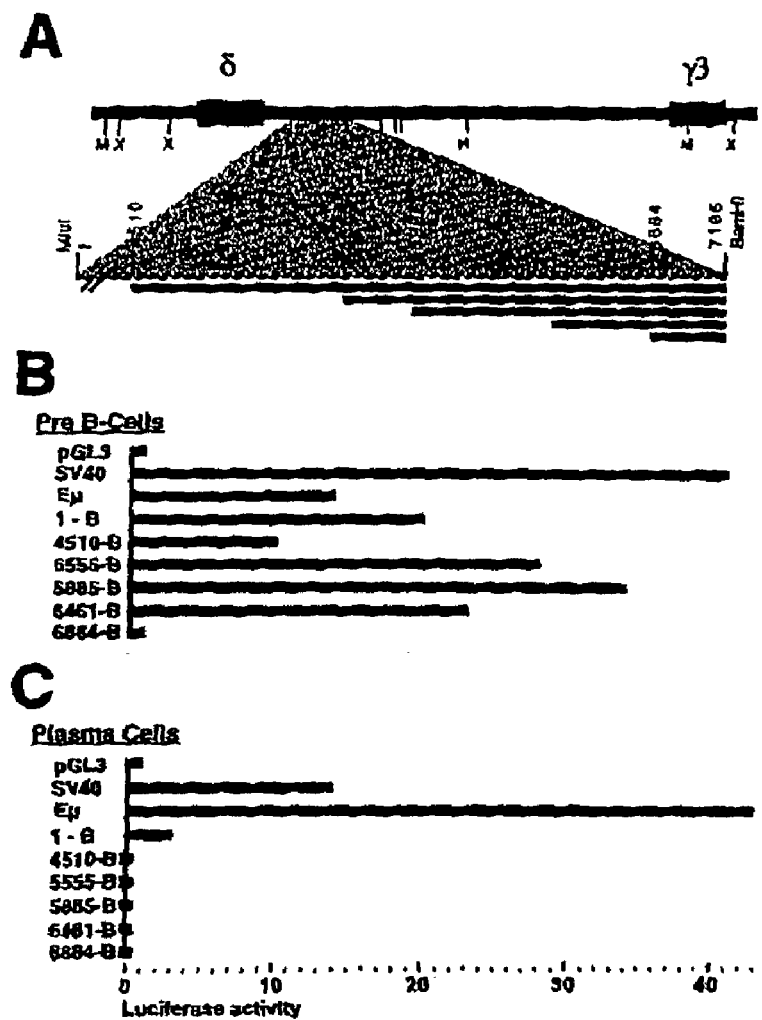
FIG. 4. Transcription enhancer activity of fragments obtained from the MluI-BamHI region of pHuIgH3'δ-γ3. A, Location of the subcloned fragments (from position 4510, 5555, 5885, 6461 and 6884 down to position 7185) with the shaded region marking the MluI-BamHI fragment (1-B), position 1 to 7185. The subcloned fragments were analysed using luciferase reporter gene assays to detect enhancer activity in B, murine pre B-cells (3-1, black bars) and human pre B-cells (NALM-6, striped bars) and C, murine plasma cells (MPC11, shaded bars) and human plasma cells (DG-75, lined bars). Experiments using murine 18-81 pre B-cells gave similarly positive results. No enhancer dependent activity was found for AH murine plasma cells, the human T lymphoblast cell line Jurkat or human KB fibroblasts (data not shown). Bars indicate luciferase activity for the different fragments: 4510-B, 5555B, 5885-B, 6461-B and 6884-B which are different length 3' clones obtained by exonuclease digest of the 1-B fragment subcloned in pGL3 (see FIG. 5). The luciferase activities were normalised to the β-galactosidase activity of the co-transfected plasmid and expressed as fold-increase. Values are averages of four to six independent experiments with at least two different DNA preparations. The range of standard deviation is shown in FIG. 5. Values were also determined for pGL3 vector alone, for pGL3 containing the SV40 promoter, and for pGL3 containing human Eμ.
Figure 5:
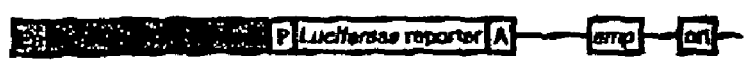
FIG. 5. Transcriptional activity of various pHuIg3'δ-γ3 fragments in combination with Eμ. A, Schematic diagram of the luciferase reporter gene construct with location of the insert fragments and position of Eμ. B, pHuIgH3'δ-γ3 map and location of the subcloned fragments (left). Transcriptional activity, with standard error indicated, of fragments 1 (MluI-HindIII), 2 (MluI-BamHI), 3 (HindIII) and 4 (BamHI) with (shaded box) and without Eμ (white box) was determined in pre B-cells and plasma cells. Assay details are described in FIG. 4 and below.
Figure 5:
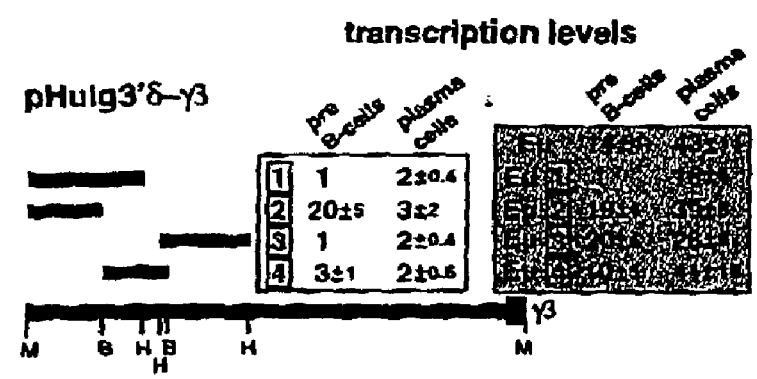

To determine any functional significance of the Cδ-Cγ3 interval in development and whether the region contained new cis-acting regulatory sequences we analysed transcriptional promoter activity of subcloned fragments from pHuIgH3'δ-γ3 using a luciferase reporter gene assay. The analysis identified a 7.2 kb MluI-BamHI fragment from the 5' Cδ proximal region which showed good enhancer activity in human and mouse pre B-cells (NALM-6 and 3-1) when placed 5' of the luciferase reporter, but did not promote luciferase activity in human or mouse plasma cells (FIGS. 4 and 5). As other fragments did not exhibit B-cell specific enhancer activity we wondered if the failure to demonstrate enhancer activity in Igb2b producing MPC11, in which the Cδ-Cγ3 intron regions are deleted, was a consequence of the IgH locus having undergone isotype switching in this cell line. This was not the case as IgM producing AH myeloma cells produced very similar results for all fragments (data not shown). In addition, the orientation of the subcloned fragments did not alter their functional activity and enhancer function of the MluI-BamHI fragment in pre B-cells was maintained in both transcriptional orientations.

To determine the precise location of this novel IgH δ-γ3 intron enhancer we dissected the MluI-BamHI fragment by MluI and exonuclease digestion which removed the 5' region and resulted in various smaller size fragments (FIG. 4A). In murine pre B-cells, enhancer activity of the whole region (position 1-7185) exceeds that of the Eμ enhancer but the most dramatic increase, twice the activity of Eμ, was obtained with a 1.3 kb fragment from position 5885 to 7185 (FIG. 4B). In comparison to mouse cells human NALM6 pre B-cells showed marked reductions in transcriptional activation. This may simply be a reflection of reduced transfection efficiencies of the human cells but could also indicate concerted interaction of several functional motifs which are recognized differently in mouse and human pre B-cells. However, the strongest transcriptional activation in both human and mouse pre B-cells was obtained by the fragment from position 5885-7185. Comparable enhancer activities, dependent on the developmental stage of the cell rather than its species of origin, agrees with what has been found for other human Ig enhancers analysed in vitro and in transgenic mice (31, 60, 61). No enhancer activity was obtained at the later developmental stage of the plasma cell (FIG. 4C). In addition, neither fibroblasts (as control cells) nor T lymphocytes showed any enhancer activity (data not shown). These results from reporter gene transfection assays define a novel region which we named Eδ-γ3 with strong cis-acting enhancer function operative at the pre B-cell stage.

A Transcription Silencer is Located Adjacent to the Enhancer

The proximity of Eμ and Eδ γ3 led us to speculate about possible enhancer cooperation during B-cell development. For this we added the human Eμ intron enhancer to 4 separate but overlapping fragments of the 21 kb sequenced 5' region of pHuIgH3'δ-γ3 and measured transcriptional activity in luciferase reporter assays (FIG. 5). It is interesting to note that except in one combination (Eμ+fragment 1) enhancer activity remained by and large as identified in single enhancer/fragment constructs analysed in B-Cell subsets. This suggests separate functions of Eμ and Eδ-γ3 and that their enhancer activities are not simply additive. Enhancer activity was maintained when Eμ was combined with fragments 2, 3 and 4 whilst the combination of Eμ with fragment 1 completely abolished enhancer activity in pre B-cells and significantly reduced enhancer activity in plasma cells (FIG. 5B). This suggests that fragment 1 contains a B-cell specific transcription silencer which is likely to be located at the 3' end of fragment 1. Fragment 4 shares a corresponding region and this may explain why transcription levels are somewhat reduced in pre B-cells when coupled to Eμ. Furthermore, fragment 1 contains the silencer in close proximity to the Eδ-γ3 enhancer identified on fragment 2. Thus, the lack of enhancer activity of fragment 1 can be explained by the presence of a strong B-cell specific silencer in this region. It emerged that further dissection of the fragments was ineffective, as Eδ-γ3 enhancer and silencer activity was reduced or abolished, and suggests that recognition motif combinations are essential. The results show that the 5'Cδ-Cγ3 region accommodates a previously unidentified B-cell specific enhancer-silencer array which may interact with Eμ to control Ig expression during developmental processes. However, the many varied sequence recognition motifs in the Cδ-Cγ3 interval, together with the coordinated enhancer interaction identified, indicate a more complex activity with perhaps other transcription modifiers.

In Transgenic Mice Eδ-γ3 is active in the developing B-cell

Figure 6:
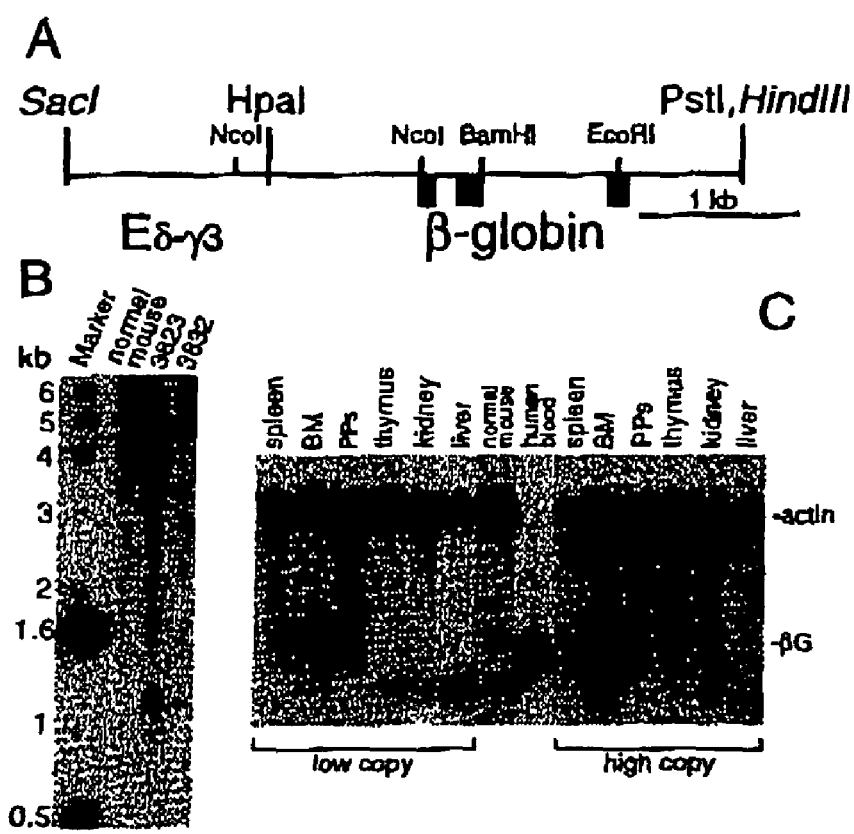
FIG. 6. Transgene construct, transgenic mouse identification and transcription analysis. A, Structure of the transgene linking Eδ-γ3 (position 5885-7185, see FIG. 4) and a human β-globin reporter gene (31). B, Southern blot hybridization of NcoI digested tail DNA from transgenic founders carrying the Eδ-γ3β-globin transgene. The internal NcoI fragment is ~1.2 kb and head to tail integration produces a ~3.2 kb band. The copy number (high copy number founder 3823, low copy number founder 3832) is reflected by the signal intensity. C, Northern blot hybridization of different tissue samples as indicated (BM, bone marrow; PPs, Peyer's patches) with the β-globin transgene (βG) and an actin probe (33) as standard. A transgene specific hybridization signal for β-globin was only found for bone marrow RNA. Human blood and normal mouse spleen RNA served as a control.

To determine in vivo specificity of the novel enhancer we constructed a transgene composed of Eδ-γ3 linked to human β-globin as a reporter gene (FIG. 6A). A high and a low copy number transgenic mouse line with head to tail integration of the transgene was identified by Southern blot (FIG. 6B) and RNA was prepared from different tissues for Northern analysis and RT-PCR. For the assays actin or HPRT transcripts were used as internal controls. In Northern hybridization we were surprised to find β-globin expression in the bone marrow and not in other B-lineage tissue (FIG. 6C) which suggests an essential role of Eδ-γ3 in B-cell development We then used RT-PCR as a more sensitive method to analyse various B-lineage, T-lineage and non-lymphoid tissues. The result was the same, the Eδ-γ3 driven transgene is silent in all non-lymphoid tissue as well as in the T-cell compartment, and extensive β-globin specific transcription is only found in bone marrow RNA, These results and the in vitro reporter gene assays suggest differentiation stage-specific activity of Eδ-γ3 from pro B-cell development (initiation of DNA rearrangement) to mature B-cell (surface IgM) prior to migration from the bone marrow.

Figure 7:
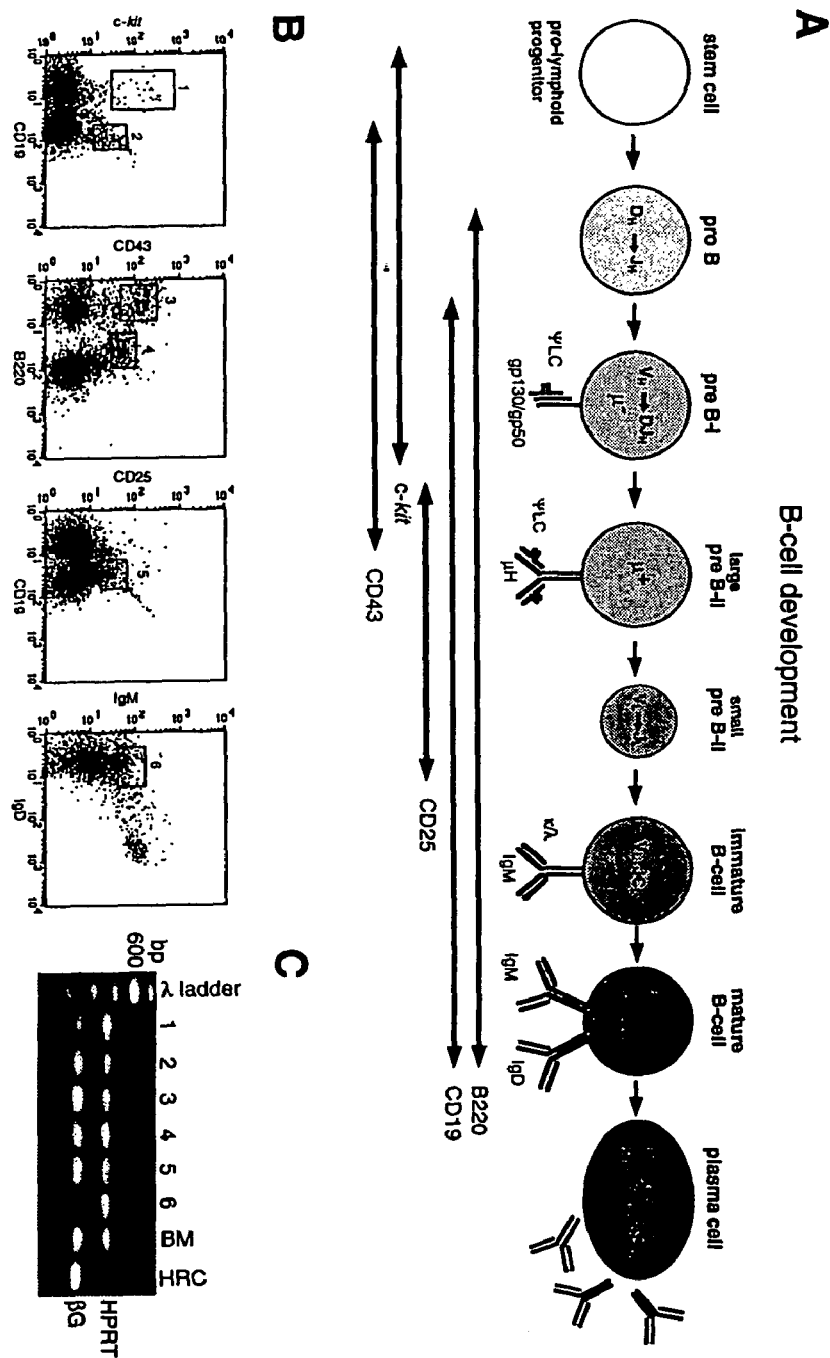
FIG. 7, Molecular characterization of B-cell subpopulations at various stages of development. A, Schematic presentation of B-cell development from stem cell to antibody secreting plasma cell. DNA rearrangement steps for the heavy chain (D to $J_H$ and $V_H$ to $DJ_H$) and the light (L) chain ($V_L$ to $J_L$) leading to surface expression and secretion of Ig are indicated. L chain rearrangement is preceded by expression of surrogate L chain (ΨLC) and gp130/gp50. Expression of the differentiation stage-specific surface markers, B220, CD19, CD25, c-kit and CD43, is indicated by arrow bars. B, Flow cytometric isolation of c-kit$^+$ CD19$^-$ [1], c-kit$^+$ CD19$^+$ [2], CD43$^+$ B220$^-$ [3], CD43$^+$ B220$^+$ [4], CD25$^+$ CD19$^+$ [5] and IgM$^+$ IgD$^-$ [6] bone marrow B-cell populations. C, RT-PCR amplification of sorted cell populations 1–6, bone marrow (bm) and human red cells (HRC) with a combination of β-globin (βG) and HPRT primers as indicated. A strong β-globin PCR product was found in B220$^+$ cells from the pro/pre B-cell type up to the immature B-cell High copy number mice were used for the analysis shown but low copy number mice gave essentially the same result.

To identify differentiation stage-specific cell populations in which Eδ-γ3 is active we used flow cytometry and RT-PCR (FIG. 7). The progressive stages in B-cell development are well characterized by cell surface markers and DNA configuration (62). We isolated several distinct cell populations from the bone marrow identified by staining with labelled antibodies specific for the B-cell markers B220 or CD19 in combination with specific antibodies for c-kit and CD43 (pro B and pre B-I stage), CD25 (pre B-II stage) and IgM/IgD (immature to mature B-cell) (FIG. 7B). RT-PCR identified β-globin activity in B220$^+$ or CD19$^-$ B-cells from bone marrow up to the immature IgM$^+$IgD$^-$ population which has completed the DNA rearrangement process. Transgene activity may be initiated at the early pro B-cell stage in c-kit$^+$ B220$^-$ cells where a faint β-globin specific PCR band (relative to the HPRT signal obtained in the same reaction) was found. As the number of c-kit$^+$CD19$^-$ cells was very low this result may have been obtained from a small cross contamination of the more abundant CD19$^+$ cell population. However, at the stage when DNA rearrangement, D to $J_H$ joining, is initiated in c-kit$^+$CD19$^+$ and CD43$^+$B220$^+$ B-cells (63) the Eδγ3 enhancer is active. H chain and largely L chain rearrangement is finalised in the immature B-cell stage and cells expressing surface IgM show that Eδγ3 driven β-globin expression is extinguished at this maturation stage. This indicates that the Eδ-γ3 enhancer is active at the earliest DNA rearrangement event and silent when the rearrangement process (V-D-J for the H chain and V-J for a L chain) has been successfully completed.

The preceding illustrative description leads to various conclusions, of certain will now be discussed.

Instability of the Cδ-Cγ3 Interval

Use of the BAC cloning system, capable of maintaining highly repetitive large insert DNA (22, 64), enabled us to establish the distance between Cδm2 and Cγ3 as 52 kb. Southern analysis and alignment of pHuIgH3'δ-γ3 with the 3' end of the HuIgH YAC (5) and the 5' end of cosIg6 (35) confirmed the overlap and identified a novel region of 11 kb. The failure of previous attempts to clone the Cδ-Cγ3 contig in cosmids or YACs can now be fully explained by the extensive repetitiveness of the intronic sequence. Such repetitive regions are prone to deletion through homologous recombination when cloned in yeast (65). It is estimated that Alu-like repeat sequences are represented on average every 4 kb throughout the genome (66, 67). In the interval from Cδm2 to Cγ3, 11 Alu-like repeats were identified in a 15 kb region. In contrast, the number of Alu motifs identified in the 950 kb region containing the variable genes of the human IgH locus was much less than expected by random distribution (68). The presence of Alu repeat elements immediately adjacent to proto-oncogene translocations has led to the suggestion that frequent Alu motifs may predispose a region as a hot spot for recombination (69, 70). Indeed, the MstII-like sequences, identified in tandem in the Cδ-Cγ3 interval, align with the consensus sequence of transposon-like elements in the human genome (39, 40). The instability of the region is further supported by linkage data, which indicate a lack of association between Cδ and Cγ3 (7) and that certain leukemias have deletion boundaries in the Cδ-Cγ3 region (9). Thus, translocations near the enhancer-silencer array in the Cδ-Cγ3 interval may result in transcriptional alterations of the rearranged genes or loci leading to a malignant phenotype of the cell subset where enhancer activity can be identified. Interestingly, chromosomal translocations in Burkitt's lymphoma where c-myc expression is deregulated by linkage to a known enhancer may represent tumors of a developmental stage in which the enhancer is active.

A Factor-Binding Site Cluster

The frequency of potential transcription factor-binding sites in the 21 kb of the Cδ-Cγ3 interval region sequenced was unexpected Using the default scores for the analysis, 0.75 for core similarity and 0.85 for matrix similarity (41) identified too many motifs to be useful. Our analysis used scores for the core similarity of 1 and matrix similarity of 0.90. This higher score allowed the unambiguous identification of multiple motifs for 9 transcription factor-binding sites, five of which are recognised by proteins that have shown to increase transcription in lymphocytes (Ikaros, E47, Oct-1, USF and Myc/Max) and four motifs shown to be recognised by transcription silencer or repressor proteins (DeltaEF1, Gfi-1, E4BP4 and C/EBPbeta). It has been shown that the repressor proteins DeltaEF1 and Gfi-1 interact with elements of the Eμ enhancer (59, 58). However, it is not obvious how the lymphocyte-specific enhancer and repressor activity identified by functional analysis of Cδ-Cγ3 interval fragments relates to this accumulation of potential transcription factor-binding motifs. Core sequence motifs for factor-binding sites found in Eμ also occur frequently in this novel enhancer region and, indeed, in the whole 21 kb region analysed (see FIG. 3). That all 9 binding sites appear frequently throughout the Eδ-γ3 interval makes it impossible to predict the activity of a particular region solely based on the nucleotide sequence. Furthermore, besides short sequence motifs no homology to draw conclusions about functional similarity was found between the MluI-HindIII fragment accommodating Eδ-γ3 and the Eμ or 3'α enhancers (71–74). Similarly, the region responsible for the transcription silencer activity could not be deduced from sequence comparison. However, because of the significance of the functional activity identified in the Cδ-γ3 interval it is unlikely that the motifs in this cluster are randomly distributed. In addition, recognition sequences essential for suppressing the function of the mouse 3' enhancer have been reported (30), but were not evident in the sequenced region. Sequence comparison of human Eδ-γ3 with the available mouse δ-γ3 interval sequence did not allow identification of an equivalent mouse enhancer, however, a reason for this could be the apparent sequence gaps.

An Essential Role of the Cδ-γ3 Interval in Early Lymphocyte Development

The location of the Cδ-Cγ3 interval means that it will be deleted after switching from Cμ to other isotypes. This implies that the regulatory activity of this region must be important during early developmental steps, which is supported by our finding that Eδ-γ3 enhancer control is operative at the pro/pre B-cell stage (see FIG. 7). Reporter gene assays suggest that the Cδ-Cγ3 interval region provides strong B-cell specific enhancer and repressor function. The strength of Eδ-γ3, position 5885-7185, can be 2-fold greater than Eμ enhancer activity in pre B-cells, but unlike Eμ and Eα3' the δ-γ3 interval enhancer does not exhibit any activity in mature B-cells. Interestingly, Eδ-γ3 activity is solely B-cell specific unlike that of Eμ which shows some activity in T-cells at the developmental timing of rearrangement (75). At developmental stages where neither the Eμ nor the E3'α enhancer was particularly active by itself, enhancer combinations identified synergistic transcriptional activity (76). A different picture emerged when Cδ-γ3 interval fragments in combination with Eμ were transfected (FIG. 5). Here individual enhancer function remained cell type-specific rather than synergistically increased, in Eδ-γ3+Eμ constructs the activity equaled that of Eδ-γ3 in pre B-cells whilst Eμ levels were obtained in plasma cells. The identified silencer extinguished both enhancers at the pre B-cell stage which suggests a complex regulatory function of elements in the Eδ-γ3 interval which appear to coordinate stage-specific H chain activation. When linked to a β-globin gene (that does not contain any cell-type-specific intragenic regulatory elements active in hematopoietic cells) and assayed in transgenic mice, Eδ-γ3 is a B-cell specific transcription enhancer element active during B-cell development in the bone marrow. This pattern of activity complements the transcriptional activities of Eμ and E3'α, contributory to V to DJ joining, switching and H chain expression (18, 21, 77, 78), and may suggest a role of Eδ-γ3 in heavy chain activation and/or initiation of DNA rearrangement. A view that the presence of several enhancers in the Ig loci simply reflects redundancy cannot be supported with these results which put the functional activity of the IgH enhancers in a possible order. Starting with the earliest; Eδ-γ3 may be important for H chain activation with initiation of DNA recombination; Eμ may then complete the joining process to allow H chain expression; Eμ may also be involved in facilitating isotype switching; Eα3' may complete the switching process, which also deletes Eμ and Eδ-γ3, and may have a role in influencing expression.

The high frequency of transcription factor-binding sites and the functional activity of the Cδ-Cγ3 intron, which includes an enhancer-silencer array, is reminiscent of the locus control regions (LCRs) described for the globin locus (79, 80). It is characteristic of LCRs that they are essential for the correct activation of a locus to ensure physiological expression levels are obtained. In transgenic mice carrying part of the human IgH locus, high level expression of the transgenes independent of copy number and integration site was not achieved (5). This suggests that neither the Eμ nor the 3' enhancer region is sufficient in itself to ensure the full activity of a single copy translocus. In transgenic mice, a translocus that includes a complete Cδ-Cγ3 interval may allow correct chromatin opening and gene activation. Identification of an equivalent region in the mouse and its removal by a knockout approach may shed further light on IgH locus activation and the DNA recombination processes which are still poorly understood.

Construction and expression analysis of the human IgH YAC have been described in Nicholson et al, J. Immunol., 163, 6898–6906, 1999. Techniques to manipulate YACs by extension have been described by Popov et al, Gene, 177, 195–201, 1996.

The extension of the HuIgH YAC by adding a (γ) 3 constant (C) region allows the study of isotype switching. We used two strategies to obtain a human IgHG3 YAC: 1) addition to the γ3 region on a cosmid to the HuIgH YAC and 2) cloning of the authentic ~50 kb region between Cδ and Cγ3 in pBAC and elongating the huIgHG3 cosmid YAC by addition of this region. This produced an ~300 kb human IgH region containing the authentic germ line region from VH2-5 to downstream of Cγ3.

Figure 8:
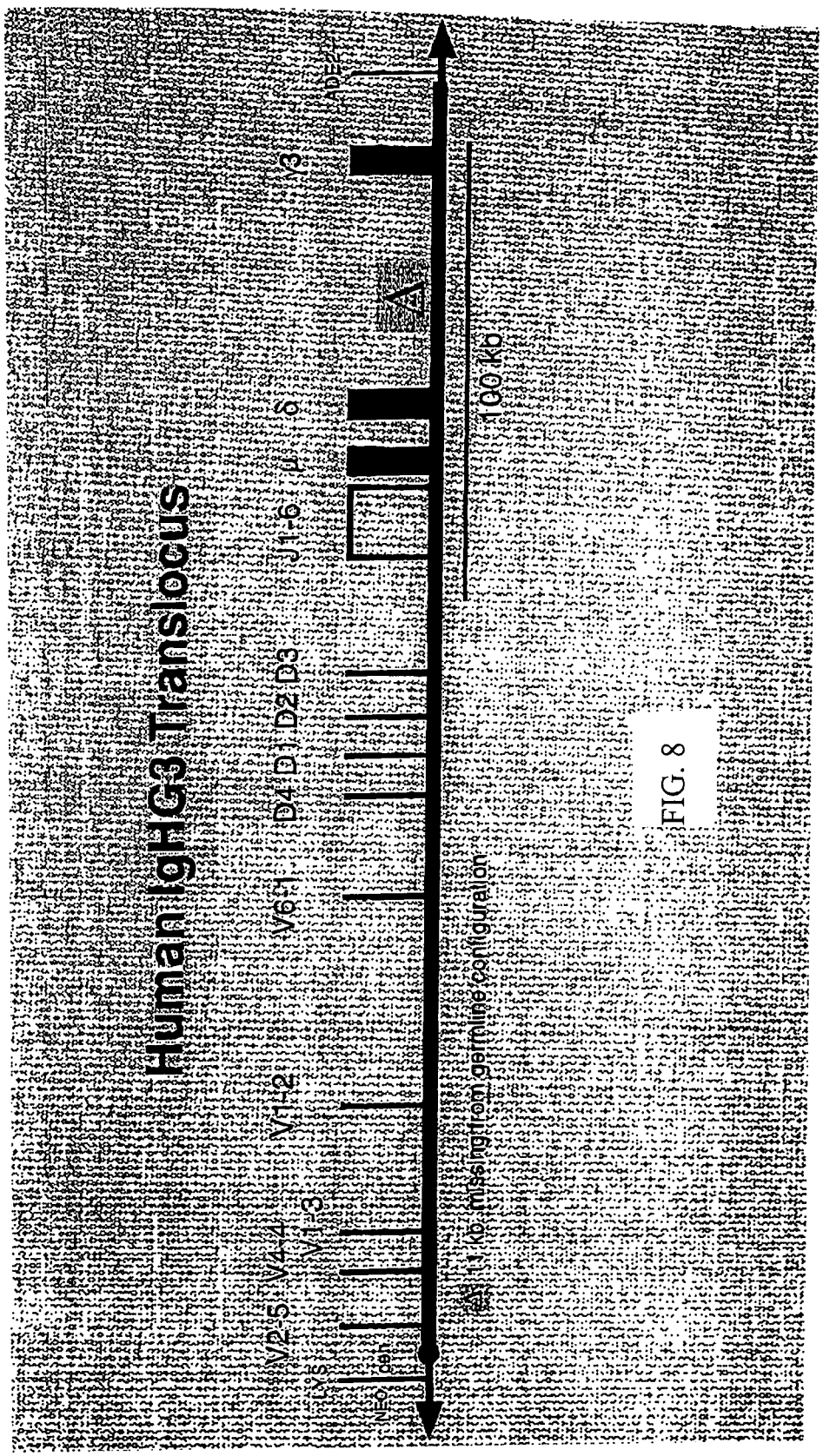
FIG. 8. Four different huIgIIG3 clones as shown in FIG. 8 were used to produce chimeric mice and also resulted in germ line transmission mice.

In detail, the experiments were done in the following way:

1) huIgH YAC-containing yeast cells were co-transfected with BssHII linearised cosIg6 (the Cγ3 containing cosmid produced by Flanagan and Rabbitts, Nature, 300, 709–713, 1983) and a non-centromeric YAC arm replacement containing ADE2 as selectable marker (Markie et al, Somat. Cell. Mol. Genet, 19, 161–169, 199). This allowed tandem integration and selection of modified YACs. IgG3 YACs were initially identified by PCR and further analysed by normal gel electrophoresis and pulsed field gel electrophoresis on Southern blots. IgH yeast clones containing the complete γ3 cosmid region in correct transcriptional orientation, integrated in the predicted way, were used in protoplast fusion of yeast and ES cells. The resulting huIgHG3 ES cell clones were further analysed for gene content. Four different huIgHG3 clones modified as shown in FIG. 8 were used to produce chimeric mice and also resulted in germ line transmission mice. Expression of human IgG3 was found in all four founders but the levels identified in ELISA assays were relatively low (ng/ml). Breeding into the μMT background (a mouse strain with silenced mouse heavy chain locus, Kitamura et al, Nature, 350, 423–426, 1991) may give more efficient human IgG3 expression.

Figure 9:
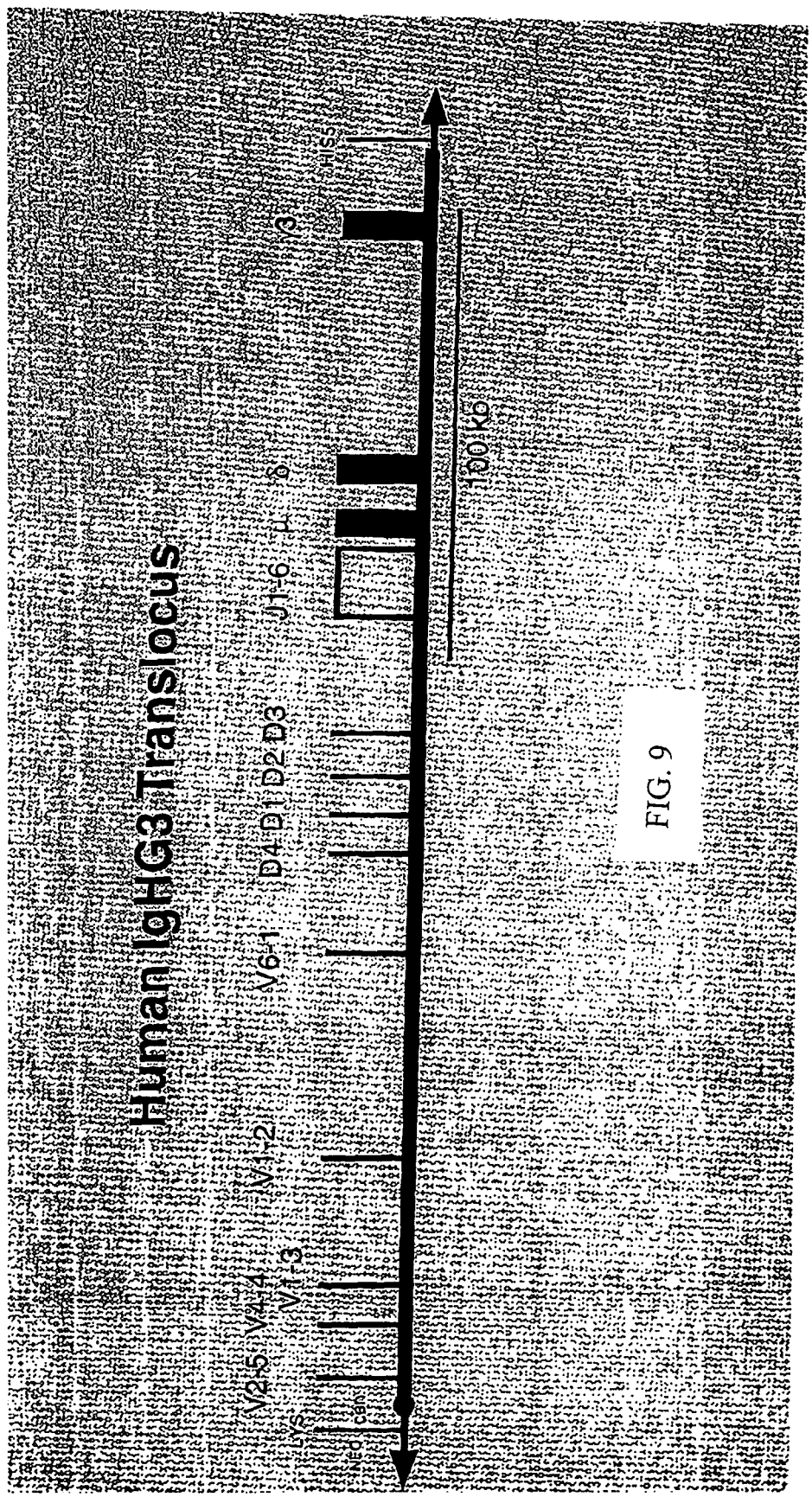
FIG. 9. Southern blot showing both genes/regions, pBAC and HIS3 in URA3, allow homologous integration into the YAC.

2) The human IgHG3 YAC with the integrated cosmid DNA contains a deletion of vital regulatory sequences identified on a pBAC clone which covers the rather unstable region between Cδ and Cγ3 (see above). In order to produce a YAC with the authentic region from the VH cluster downstream of the γ constant region genes we co-transformed the cosmid containing γ3 YAC with the MluI linearised pBAC and the HIS5 gene as a selectable marker (Nishiwaki et al, Mol. Gen Genet., 208, 159–167, 1987). The HIS5 gene was subcloned into URA3, a gene present on the non-centromeric YAC arm. Both genes/regions, pBAC and HIS3 in URA3, allow homologous integration into the YAC and correct integration was identified by PCR and Southern blot (FIG. 9). YAC-ES cell protoplast fusion was carried out and the resulting clones were analysed by Southern blot and PCR. Two clones were used to obtain chimeric mice which may be bred to obtain germ line transmission.

REFERENCES

1. Hofker, M. H., M. A. Walter and D. W. Cox 1989. Complete physical map of the human immunoglobulin heavy chain constant region gene complex *Proc. Natl. Acad. Sci. USA* 66:507.

2. Mendez, M. J., H. Abderrahim, M. Noguchi, N. E. David, M. C. Hardy, L. L. Green, H. Tsuda, S. Yoast, C. E. Maynard-Currie, D. Garza, R. Gemmill, A. Jakobovits, and S. Klapholz. 1995. Analysis of the structural integrity of YACs comprising human immunoglobulin genes in yeast and in embryonic stem cells. *Genomics* 26:294.

3. Chen, C. and B. K. Birshtein. 1997. Virtually identical enhancers containing a segment of homology to murine 3' IgH-E(hs1,2) lie downstream of human Ig Cα1 and Cα2 genes. *J. Immunol.* 159:1310.

4. Kang, H. K. and D. W. Cox 1996. Tandem repeats 3' of the IGHA genes in the human immunoglobulin heavy chain gene cluster, *Genomics* 35:189.

5. Brüggemann, M. and M. S. Neuberger. 1996. Strategies for expressing human antibody repertoires in transgenic mice. *Immunol. Today* 17:391.

6. Green, L. L. M. C. Hardy, C. E. Maynard-Currie, H. Tsuda, D. M. Louie, M. J. Mendez, H. Abderrahim, M. Noguchi, D. H. Smith, Y. Zeng, N. E. David, H. Sasai, D. Garza, D. G. Brenner, J. F. Hales, R. P. McGunness, D. J. Capon, S. Klapholz and A. Jakobovits. 1994. Antigen-specific human monoclonal antibodies from mice engineered with human Ig heavy and light chain YACs. *Nature Genetics* 7:13.

7. Benger, J. C. and D. W. Cox 1989. Polymorphisms of the immunoglobulin heavy-chain delta gene and association with other constant-region genes. *Am. J. Hum. Genet.* 45:606.

8. Walter, M. A. and D. W. Cox 1991. Nonuniform linkage disequilibrium within a 1,500-kb region of the human immunoglobulin heavy-chain complex *Am. J. Hum. Genet.* 49:917.

9. Dyer, M. J. S., J. M. Heward, V. J. Zani, V. Buccheri and D. Catovsky. 1993. Unusual deletions within the immunoglobulin heavy-chain locus in acute leukemias. *Blood* 82:865.

10. Shimizu, A. N. Takahashi, Y. Yaoita and T. Honjo. 1982. Organization of the constant-region gene family of the mouse immunoglobulin heavy chain. *Cell.* 28:499.

11. Cockerill, P. N. 1990. Nuclear matrix attachment occurs in several regions of the IgH locus. *Nucl. Acids Res.* 18:2643.

12. Lieberson, R., J. Ong, X. Shi and L. A. Eckhardt. 1995. Immunoglobulin gene transcription ceases upon deletion of a distant enhancer. *EMBO J.* 14:6229.

13. Michaelson, J. S., M. Singh, C. M. Snapper, W. C. Sha, D. Baltimore and S. K. Birshtein. 1996. Regulation of 3' IgH enhancers by a common set of factors, including κB-Binding proteins. *J. Immunol.* 156:2828.

14. Rao, E., G. Gang and R. Sen. 1997. The three-protein-DNA complex on a B cell-specific domain of the immunoglobulin μ heavy chain gene enhancer. *J Biol. Chem.* 272: 6722.

15. Mac, E. E. 1999. Immunoglobulins: molecular genetics. in *Fundamental Immunology, Fourth Edition,* ed. W. E. Paul, publ. Lippincott-Raven, Philadelphia, pp. 111–182.

16. Grant, P. A., V. Arulampalam, L. Ahrlund-Richter and S. Pettersson. 1992. Identification of Ets-like lymphoid specific elements within the immunoglobulin heavy chain 3' enhancer. *Nucl. Acids Res.* 20:4401.

17. Arulampalam, V., L. Eckhardt and S. Pettersson. 1997. The enhancer shift: a model to explain the developmental control of IgH gene expression in B-lineage cells. *Immunol. Today* 18:549.

18. Cogné, M., R. Lansford, A. Bottaro, J. Zhang, J. Gorman, F. Young, H. Cheng and F. W. Alt. 1994. A class switch control region at the 3' end of the immunoglobulin heavy chain locus. Cell 77:737.

19. Ernst, P. and S. T. Smale. 1995. Combinatorial Regulation of Transcription II: The immunoglobulin μ heavy chain gene. *Immunity* 2:427.

20. Henderson, A. and K. Calame. 1998. Transcriptional Regulation During B Cell Development. *Annu. Rev. Immunol.* 16:163.

21. Serwe, M. and F. Sablitzky. 1993. V(D)J recombination in B cells is impaired but not blocked by targeted deletion of the immunoglobulin heavy chain intron enhancer. *EMBO J.* 12:2321.

22. Kim, U.-J., S. W. Birren, T. Slepak V. Mancino, C. Boysen, H.-L. Kang, M. I. Simon and H. Shizuya. 1996. Construction and characterization of a human bacterial artificial chromosome library. *Genomics* 34:213.

23. Eagle, H. 1955. Propagation in a fluid medium of a human epidermold carcinoma strain, KB. *Proc. Soc. Exp. Biol.* 89:362.

24. Sheng, Y., V. Mancino and B. Birren. 1995. Transformation of *Escherichia coli* with large DNA molecules by electroporation. *Nucl. Acids Res.* 23:1990.

25. Bützler, C., X. Zou, A. V. Popov and M. Brüggemann. 1997. Rapid induction of B-cell lymphomas in mice carrying a human IgH/c-myc YAC. *Oncogene* 14:1383.

26. Brüggemann, M., G. T. Williams, C. I. Bindon, M. R. Clark M. R. Walker, R. Jefferis, H. Waldmann and M. S. Neuberger. 1987. Comparison of the effector functions of human immunoglobulins using a matched set of chimeric antibodies. *J. Exp. Med.* 166:1351.

27. Mae, E., M. Fougereau, J.-N. Argenson, J.-M. Aubaniac and C. Schiff. 1996. Cell surface expression of surrogate light chain (ΨL) in the absence of μ on human pro-B cell lines and normal pro-B cells. *Eur. J. Immunol.* 26:2172.

28. Sideras, P., L. Nilsson, K. B. Islam, I. Zalcberg, Q. L. Freihof, A. Rosén, G. Juliusson, L. Hammarström ans C. I. E. Smith. 1992. Transcription of unrearranged IgH chain genes in human B cell malignancies. *J. Immunol.* 149:244.

29. Weiss, A., R. L. Wiskocil and J. D. Stobo. 1984. The role of T3 surface molecules in the activation of human T cells: A two-stimulus requirement for IL2 production reflects events occurring at a pre-translational level. *J. Immunol.* 133:123.

30. Singh, M. and B. K. Birshtein. 1993. NF-HB (BSAP) is a repressor of the murine immunoglobulin heavy-chain 3'α enhancer at early stages of B-cell differentiation. *Mol. Cell. Biol.* 13:3611.

31. Meyer, K. B., Y.-M. Teh and M. S. Neuberger. 1996. The Igk 3' enhancer triggers gene expression in early B lymphocytes but its activity is enhanced on B cell activation. *Int. Immunol.* 8:1561.

32. Gordon, J. W. and F. H. Ruddle. 1983. Gene transfer into mouse embryos: production of transgenic mice by pronuclear injection. *Methods Enzymol.* 101:411.

33. Palomo, C., X. Zou, I. C. Nicholson, C. Bützler and M. Brüggemann. 1999. B-cell tumorigenesis in mice carrying a YAC-based IgH/c-myc translocus is independent of Eμ. *Cancer Res.* 59:5625.

34. Popov, A. V., X. Zou, J. Xian, I. C. Nicholson and M. Brüggemann. 1999. A human immunoglobulin λ locus is similarly well expressed in mice and humans. *J. Exp. Med.* 189:1611.

35. Flanagan, J. G. and T. H. Rabbitts. 1982. Arrangement of human immunoglobulin heavy chain constant region genes implies evolutionary duplication of a segment containing γ, ε and α genes. *Nature* 300:23.

36. Huck, S., P. Fort, D.-H Crawford, M.-P. Lefranc and G. Lefranc. 1986. Sequence of a human immunoglobulin gamma 3 heavy constant region gene; comparison with the other human Cγ genes. *Nucl. Acids Res.* 14:1779.

37. Deininger, P. L., D. J. Jolly, C. M. Rubin, T. Friedmann and C. W. Schmid. 1981 Base sequence studies of 300 nucleotide renatured repeated human DNA clones. *J. Mol. Biol.* 151:17

38. Boeke, J. D. 1997. LINEs and Alus-the poly A connection. *Nat Gen.* 16:6.

39. Fields, C. A., D. L. Grady and R. K. Moyzis. 1992. The human THE-LTR(O) and MstII interspersed repeats are subfamilies of a single widely distributed highly variable repeat family. *Genomics* 13:431.

40. Mermer, B., M. Colb and T. G. Krontiris. 1987. A family of short, interspersed repeats is associated with tandemly repetitive DNA in the human genome. *Proc. Natl. Acad. Sci. USA* 84:3320.

41. Frech, K., K. Quandt and T. Werner. 1997. Finding protein-binding sites in DNA sequences: the next generation. *TIBS* 22:103.

42. Ghosh, D. 1993. Status of the transcription factors database (TFD). *Nucl. Acids Res.* 21:3117.

43. Fitzsimmons, D. and J. Hagman. 1996. Regulation of gene expression at early stages of B-cell and T-cell differentiation. *Curr. Opin. Immunol.* 8: 166.

44. Glimcher, L. H. and H. Singh. 1998. Transcription factors in lymphoid development-T and B cells get together. *Cell* 96:13.

45, Bendall, A. J. and P. L. Molloy. 1994. Base preferences for DNA binding by the bHLH-zip protein USF: effects of $MgCl_2$ on specificity and comparison with binding of Myc family members. *Nucl. Acids Res.* 22:2601.

46. Georgopoulos, K. 1997. Transcription factors required for lymphoid lineage commitment. *Curr. Opin. Immunol.* 9:222.

47. Grandori, C. and R. N. Eisenman. 1997. Myc target genes. *TIBS* 22:177.

48. Kadesch, T. 1992. Helix-loop-helix proteins in the regulation of immunoglobulin gone transcription. *Immunol. Today* 13:31.

49. Li, P., X. He, M. R. Gerrero, M. Mok, A. Aggarwal and M. G. Rosenfeld. 1993. Spacing and orientation of bipartite DNA-binding motifs as potential functional determinants for POU domain factors. *Genes Dev.* 7: 2483.

50. Zwilling, S., A. Annweiler and T. Wirth. 1994. The POU domains of the Oct1 and Oct2 transcription factors mediate specific interaction with TBP. *Nucl. Acids Res.* 22:1655.

51. Solomon, D. L., C., B. Arnati and H. Land. 1993. Distinct DNA binding preferences for the c-Myc/Max and Max/Max dimers. *Nucl. Acids Res.* 21: 5372.

52. Molnár, A. and K. Georgopoulos. 1994. The Ikaros gene encodes a family of functionally diverse zinc finger DNA-binding proteins. *Mol. Cell. Biol.* 14:8292.

53. Klug, C. A., S. J. Morrison, M. Masek, K. Hahm, S. T. Smale and I. L. Weissman. 1998. Hematopoietic stem cells and lymphoid progenitors express different Ikaros isoforms, and Ikaros is localized to heterochromatin in immature lymphocytes. *Proc. Natl. Acids Sci. USA* 95:657.

54. Cowell, I. G., A. Skinner and H. C. Hurst. 1992. Transcriptional repression by a novel member of the bZIP Family of transcription factors. *Mol. Cell. Biol.* 12:3070, 55. Lu, M., J. Seufert and J. F. Hebener, 1997. Pancreatic beta-cell-specific repression of insulin gene transcription by CCAAT/enhancer-binding protein beta. Inhibitory interactions with basic helix-loop-helix transcription factor E47. *J. Biol. Chem.* 272:28349.

56. Sekido, R., K. Murai, J.-I. Funahashi, Y. Kamachi, A. Fujisawa-Sehara, Y.-I. Nabeshima and H. Kondoh. 1994. The δ-Crystallin enhancer-binding protein δEF1 is a repressor of E2-box-mediated gene activation. *Mol. Cell Biol.* 14:5692.

57. Sekido, R., T. Takagi, M. Okanami, H. Moride, M. Yamamura, Y. Higashi and H. Kondoh. 1996. Organisation of the gene encoding transcriptional repressor deltaEF1 and cross-species conservation of its domains. *Gene* 16:227.

58. Zweidler-McKay, P. A., H. L. Grimes, M. M. Flubacher and P. N. Tsichlis. 1996. Gfi-1 Encodes a Nuclear Zinc finger protein that binds DNA and functions as a transcriptional repressor. *Mol. Cell Biol.* 16:4024

59. Grimes, H. L., T. O. Chan, P. A. Zweidler-McKay, B. Tong and P. N. Tsichlis. 1996. The Gfi-1 proto-oncoprotein contains a novel transcriptional repressor domain, SNAG, and inhibits G1 arrest induced by interleukin-2 withdrawal. *Mol. Cell. Biol.* 16:6263.

60. Enjoji, M. 1994. Human HE2 (μB) and μA motifs show the same function as whole IgH intronic enhancer in transgenic mice. *Mol. Cell. Biochem.* 137:33.

61. Stevens, S., P. Ordentlich, R. Sen and T. Kadesch. 1996. HMG box-activating factors 1 and 2, two HMG box transcription factors that bind the human Ig heavy chain enhancer. *J. Immunol.* 157:3491.

62. Hardy, R. R., C. E. Carmack, S. A. Shinton, J. D. Kemp and K. Hayakawa. 1991. Resolution and characterization of pro-B and pre-pro-B cell stages in normal mouse bone marrow. *J. Exp. Med.* 173:1213.

63. ten Boekel, E., F. Melchers and A. Rolink. 1995. The status of Ig loci rearrangements in single cells from different stages of B cell development *Int. Immunol.* 7:1013.

64. Wang, M., X.-N. Chen, S. Shouse, J. Manson, Q. Wu, R. Li, J. Wrestler, D. Noya, Z.-G. Sun, J. Korenberg and E. Lai. 1994. Construction and characterization of a human chromosome 2-specific BAC library. *Genomics* 24:527.

65. Le, Y. and M. J. Dobson. 1997. Stabilization of yeast artificial chromosome clones in a rad54-3 recombination decent host strain. *Nucl. Acids Res.* 25:1248.

66. Sherry, S. T., H. C. Harpending, M. A. Batzer and M. Stoneking. 1997. Alu evolution in human populations: using the coalescent to estimate effective population size. *Genetics* 147:1977.

67. Yulug, I. G., A. Yulug and E. M. C. Fisher. 1995. The frequency and position of Alu repeats in cDNAs, as determined by database searching. *Genomics* 27:544.

68. Matsuda, F., K. Ishii, P. Bourvagnet, K. Kuma, H. Hayashida, T. Miyata and T. Honjo. 1998. The complete nucleotide sequence of the human immunoglobulin heavy chain variable region locus *J. Exp. Med.* 188:2151.

69. Jeffs, A. R., S. M. Benjes, T. L. Smith, S. J. Sowerby and C. M. Morris. 1998. The SCR gene recombines preferentially with Alu elements in complex BCR-ABL translocations of chronic myeloid leukaemia *Hum. Mol. Gen.* 7:767.

70. Willis, T. G., D. M. Jadayel, L. J. A. Coignet, M. Abdul-Rauf, J. G. Treleaven, D. Catovsky and M. J. Dyer. 1997. Rapid molecular cloning of rearrangements of the IGHJ locus using long-distance inverse polymerase chain reaction. *Blood* 90:2456.

71. Carter, R. S., P. Ordentlich and T. Kadesch. 1997. Selective utilisation of basic helix-loop-helix-leucine zipper proteins at the immunoglobulin heavy-chain enhancer. *Mol. Cell. Biol.* 17:18.

72. Glozak, M. A. and B. Blomberg. 1996. The human λ immunoglobulin enhancer is controlled by both positive elements and developmentally regulated negative elements. *Mol. Immunol.* 33:427.

73. Gumucio, D. H., H. Heilstedt-Williamson, T. A. Gray, S. A. Tarlé, D. A. Shelton, D. A. Tagle, J. L. Slightom, M. Goodman and F. S. Collins. 1992. Phylogenetic footprinting reveals a nuclear protein which binds to silencer sequences in the human γ and ε globin gene. *Mol. Cell. Biol.* 12:4919.

74. Scheuermann, R. H. and U. Chen. 1989. A developmental-specific factor binds to suppressor sites flanking the immunoglobulin heavy-chain enhancer. *Genes Dev.* 3:1255.

75. Cook, G. P., K. B. Meyer, M. S. Neuberger and S. Pettersson. 1995. Regulated activity of the IgH intron enhancer (Eδ) in the T lymphocyte lineage. *Int. Immunol.* 7: 89.

76. Ong, J., S. Stevens, R. G. Roeder and L. A. Eckhardt 1998. 3′ IgH Enhancer elements shift synergistic interactions during B cell development. *J. Immunol,* 160:4896.

77. Bottaro, A., F. Young, J. Chen, M. Serwe, F. Sablitzky and F. W. Alt. 1998. Deletion of the IgH intronic enhancer and associated matrix-attachment regions decreases, but does not abolish, class switching at the μ locus. *Int. Immunol.* 10:799.

78. Manis, J. P., N. van der Stoep, M. Tian, R. Ferrini, L. Davidson, A. Bottaro and F. W. Alt. 1998. Class switching in B cells lacking 3' immunoglobulin heavy chain enhancers. *J. Exp. Med.* 188:1421.

79. Fraser, P. and F. Grosveld. 1998. Locus control regions, chromatin activation and transcription *Cur. Opin. Cell Biol.* 10:361.

80. Townes, T. M. and R. R. Behringer. 1990. Human globin locus activation region (LAR): role in temporal control. *Trends in Genetics* 6:219.

81. Hahm, K., P. Ernst, K. Lo, G. S. Kim and S. T. Smale. 1994. The lymphoid transcription factor LyF-1 is encoded by specific, alternatively spliced mRNAs derived from the Ikaros gene. *Mol. Cell. Biol.* 14;7111.

82. Lo, K., N. R. Landau and S. T. Smale. 1991. LyF-1, a transcriptional regulator that interacts with a novel class of promoters for lymphocyte-specific genes. *Mol. Cell. Biol.* 11:5229.

83. Sigvardsson, M., M. O'Riordan and R. Grosschedl. 1997. EBS and E47 collaborate to induce expression of the endogenous immunoglobulin surrogate light chain genes. *Immunity* 7:25.

84. Staudt, L. M. and M. J. Lenardo. 1991. Immunoglobulin Gene Transcription. *Annu. Rev. Immunol,* 9:373.

85. Verrijzer, C. P., M. J. Alkema, W. W. van Weperen, H. C. Van Leeuwen, M. J. J. Strating and P. C. van der Vliet. 1992. The DNA binding specificity of the bipartite POU domain and its subdomains. *EMBO J.* 11:4993.

86. Ikushima, S., T. Inukai, T. Inaba, S. D. Nimer, J. L. Cleveland and A. T. Cook. 1997. Pivotal role for the NFIL3/E4BPA transcription factor in interleukin 3-mediated survival of pro-B lymphocytes. *Proc. Natl. Acad. Sci. USA* 94:2609.

87. Zhang, W., J. Zhang, M. Komuc, K. Kwan, R. Frank and S. D. Nimer. 1995. Molecular cloning and characterization of NF-IL3A, a transcriptional activator of the human interleukin-3 promoter. *Mol. Cell. Biol.* 15:6055.

88. Saisanit, S. and X.-H. Sun. 1997. Regulation of the pro-B-cell-specific enhancer of the Id1 gene involves the C/EBP family of proteins. *Mol. Cell. Biol.* 17:844.

Abbreviations used herein: BAC, bacterial artificial chromosome; LCR, locus control region; MAR, matrix association region; PFGE, pulsed field gel electrophoresis; YAC, yeast artificial chromosome.

What is claimed is:

1. An artificial chromosome comprising a first polynucleotide sequence that regulates gene expression wherein said first polynucleotide sequence consists of the 1.3 kb polynucleotide sequence from position 5885 to 7185 between Cδ and Cγ3 of the human IgH locus; and wherein said artificial chromosome further comprises a heterologous gene under the control of said first polynucleotide sequence.

2. The chromosome according to claim 1, selected from the group consisting of bacterial, yeast, eukaryotic and mammalian chromosomes.

3. The chromosome according to claim 1, which includes a polynucleotide sequence encoding a transcription-binding factor.

* * * * *